(12) United States Patent
Kostrzewski

(10) Patent No.: US 8,080,018 B2
(45) Date of Patent: Dec. 20, 2011

(54) DISPOSABLE CIRCUMCISION DEVICE

(75) Inventor: Stanislaw Kostrzewski, Newtown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 156 days.

(21) Appl. No.: 12/689,460

(22) Filed: Jan. 19, 2010

(65) Prior Publication Data
US 2011/0178528 A1    Jul. 21, 2011

(51) Int. Cl.
*A61B 17/32* (2006.01)

(52) U.S. Cl. ........................................ 606/118; 606/144

(58) Field of Classification Search .................. 606/118, 606/139, 144, 148, 149, 153, 232; 227/180.1
See application file for complete search history.

(56) References Cited

U.S. PATENT DOCUMENTS

| | | | | | |
|---|---|---|---|---|---|
| 1,417,142 | A | * | 5/1922 | Couch | 606/118 |
| 1,577,054 | A | * | 3/1926 | Berkmann | 606/144 |
| 1,765,319 | A | * | 6/1930 | Williams | 606/118 |
| 2,638,901 | A | * | 5/1953 | Sugarbaker | 606/153 |
| 3,040,748 | A | * | 6/1962 | Klein et al. | 606/149 |
| 3,048,177 | A | * | 8/1962 | Takaro | 606/153 |
| 3,057,355 | A | * | 10/1962 | Smialowski et al. | 606/149 |
| 3,111,124 | A | * | 11/1963 | Rodbard | 606/118 |
| 3,473,533 | A | * | 10/1969 | Freda | 606/118 |
| 4,207,898 | A | * | 6/1980 | Becht | 227/179.1 |
| 4,491,136 | A | * | 1/1985 | LeVeen | 606/118 |
| 4,553,543 | A | * | 11/1985 | Amarasinghe | 606/148 |
| 5,163,943 | A | * | 11/1992 | Mohiuddin et al. | 606/118 |
| 5,320,632 | A | * | 6/1994 | Heidmueller | 606/144 |
| 5,360,154 | A | * | 11/1994 | Green | 227/179.1 |
| 5,439,466 | A | * | 8/1995 | Kilejian | 606/118 |
| 5,545,171 | A | * | 8/1996 | Sharkey et al. | 606/148 |
| 5,649,933 | A | * | 7/1997 | Singh | 606/118 |
| 5,881,943 | A | * | 3/1999 | Heck et al. | 227/176.1 |
| 5,904,697 | A | * | 5/1999 | Gifford et al. | 606/155 |
| 6,066,160 | A | * | 5/2000 | Colvin et al. | 606/232 |
| 6,355,050 | B1 | * | 3/2002 | Andreas et al. | 606/144 |

(Continued)

FOREIGN PATENT DOCUMENTS

CN    201 119 892 Y    9/2008

(Continued)

OTHER PUBLICATIONS

European Search Report for EP 11250055.8-1269 date of completion is May 18, 2011 (3 pages).

*Primary Examiner* — Gary Jackson
*Assistant Examiner* — David Eastwood

(57) ABSTRACT

A circumcision system for removing excess foreskin from a penis is disclosed and includes includes a housing, an actuation mechanism, and an anvil. The housing has a threaded hole that defines a longitudinal axis and a locking ring. The locking ring has an internal thread. The actuation mechanism extends through the threaded hole and has a series of needles. A suture is removably attached to a distal end of each of the series of needles. Each of the series of needles has a tapered end and a groove through the tapered end configured to accept and detachably retain the suture. A knife is connected to the actuation mechanism. The knife has a circular blade. The anvil has a passage that is co-axially located with the longitudinal axis and an external thread that is configured to be complimentary to the internal thread. The anvil is in the shape of a collar.

16 Claims, 11 Drawing Sheets

U.S. PATENT DOCUMENTS

| | | | |
|---|---|---|---|
| 6,660,012 B2 * | 12/2003 | Lahiji | 606/118 |
| 6,746,456 B2 * | 6/2004 | Xiao | 606/144 |
| 6,939,356 B2 * | 9/2005 | Debbas | 606/144 |
| 7,128,748 B2 * | 10/2006 | Mooradian et al. | 606/151 |
| 7,141,055 B2 * | 11/2006 | Abrams et al. | 606/115 |
| 7,175,660 B2 * | 2/2007 | Cartledge et al. | 623/2.11 |
| 7,285,125 B2 * | 10/2007 | Viola | 606/153 |
| 7,303,567 B1 | 12/2007 | Smith | |
| 7,318,830 B2 * | 1/2008 | Mayoral | 606/139 |
| RE40,377 E * | 6/2008 | Williamson et al. | 623/2.11 |
| 7,726,539 B2 * | 6/2010 | Holsten et al. | 227/179.1 |
| 7,879,044 B2 * | 2/2011 | Tomlinson | 606/118 |
| 7,935,129 B2 * | 5/2011 | Gifford et al. | 606/153 |
| 2001/0021856 A1 * | 9/2001 | Bolduc et al. | 606/144 |
| 2002/0020732 A1 * | 2/2002 | Adams et al. | 227/180.1 |
| 2002/0065524 A1 * | 5/2002 | Miller et al. | 606/139 |
| 2002/0082625 A1 * | 6/2002 | Huxel et al. | 606/153 |
| 2002/0095164 A1 * | 7/2002 | Andreas et al. | 606/144 |
| 2002/0111639 A1 * | 8/2002 | Armstrong | 606/144 |
| 2003/0065336 A1 * | 4/2003 | Xiao | 606/144 |
| 2003/0176872 A1 * | 9/2003 | Lahiji | 606/118 |
| 2004/0068273 A1 * | 4/2004 | Fariss et al. | 606/144 |
| 2004/0084505 A1 * | 5/2004 | Bilotti et al. | 227/180.1 |
| 2004/0186490 A1 * | 9/2004 | Gifford et al. | 606/153 |
| 2004/0195289 A1 * | 10/2004 | Aranyi | 227/180.1 |
| 2004/0215210 A1 * | 10/2004 | Duel | 606/118 |
| 2005/0043746 A1 * | 2/2005 | Pollak et al. | 606/144 |
| 2005/0131430 A1 * | 6/2005 | Ravikumar | 606/144 |
| 2005/0216038 A1 * | 9/2005 | Meade et al. | 606/144 |
| 2005/0228407 A1 * | 10/2005 | Nobles et al. | 606/144 |
| 2005/0228414 A1 * | 10/2005 | Mayoral | 606/153 |
| 2006/0122626 A1 | 6/2006 | Duel | |
| 2006/0167476 A1 * | 7/2006 | Burdulis et al. | 606/144 |
| 2008/0004631 A1 | 1/2008 | Tomlinson | |
| 2008/0021482 A1 | 1/2008 | Tomlinson | |
| 2008/0161832 A1 * | 7/2008 | Bauman et al. | 606/148 |
| 2008/0195116 A1 * | 8/2008 | Mansour | 606/118 |
| 2009/0026245 A1 * | 1/2009 | Holsten et al. | 227/180.1 |
| 2009/0048613 A1 * | 2/2009 | Surti | 606/139 |
| 2009/0120994 A1 * | 5/2009 | Murray et al. | 227/180.1 |

FOREIGN PATENT DOCUMENTS

| | | |
|---|---|---|
| CN | 201 227 313 Y | 4/2009 |
| CN | 101 884 559 A | 11/2010 |

* cited by examiner

DISPOSABLE CIRCUMCISION DEVICE

BACKGROUND

1. Technical Field

This application generally relates to the field of circumcision. More particularly, the present disclosure relates to a method and a device for surgical removal of the excess foreskin or prepuce from the penis by a non-traumatic approach and retention of sutures within the circumcised penis.

2. Related Art

The conventional circumcision is usually performed by a surgical team consisting of a surgeon and at least one assistant. The team severs the excessive foreskin, which covers glans of the penis, and sutures the cut edge of the foreskin. The average operating time that a conventional circumcision operation consumes is approximately half an hour, a time period considered relatively long for an operation.

The conventional circumcision clamp has another disadvantage in that it causes severe bleeding during the surgery. Generally, most patients experience apprehension during a circumcision operation. During the operation, the patient's penis is almost in a naturally flaccid state.

SUMMARY

The present disclosure is directed to a disposable circumcision device for surgically removing excess foreskin or prepuce from a penis. The disposable circumcision device includes a housing, an actuation mechanism, and an anvil.

The housing has a threaded hole that defines a longitudinal axis and a locking ring. The locking ring has an internal thread.

The actuation mechanism includes a jacking screw that extends through the threaded hole.

A cartridge is rotatably attached to the distal end of the actuation mechanism. The actuation mechanism is able to provide longitudinal movement of the cartridge with respect to the housing. The cartridge has a series of needles that removably hold a suture. The suture is removably retained in a distal end of each of the series of needles. Each of the series of needles has a tapered end and a groove through the tapered end that accepts and detachably retains the suture. Each of the grooves in the series of needles is aligned circularly to accept a suture in the shape of a ring.

A knife is connected with the actuation mechanism. The knife has a circular blade.

The anvil has a passage that is co-axially located with the longitudinal axis and an external thread that is complimentary to the internal thread of the locking ring. The anvil is in the shape of a collar. The anvil has a series of access windows and a cutting ring.

At least one suture retainer is releasably attached to the anvil. The suture retainer has a passageway. The passageway includes a substantially cylindrical bore and two diametrically opposed slots extending radially outward therefrom. The substantially cylindrical bore removably accepts one of the needles therethrough. The diametrically opposed slots have a restricted section that secures the suture within the suture retainer during insertion of and after removal of the needles from the suture retainer.

The anvil has a first section and a second section. Each of the first and second sections are complementary fragments that mount together to form the shape of the collar. The first section of the anvil has at least one male fitting and the second section of the anvil has at least one female fitting. The female fitting accepts and releasably retains the male fitting. A portion of the external thread is formed about a proximal end of each of the first and second sections of the anvil.

The housing has a stop that prevents the external thread from penetrating past a predetermined depth into the housing. The housing has an external surface. The anvil has an internal surface that complements, intimately with the external surface of the housing. The housing has at least one guide groove that ensures proper positioning of the anvil with respect to the series of needles.

Both the suture and the suture retainer may be constructed from a biocompatible material that is absorbable.

To cover the full range of penis sizes it is possible to provide more then one size of the instrument in a kit.

A method of use of the disposable circumcision device is also provided. The surgeon is provided with the disposable circumcision device. The two anvil halves are snapped together and slid down over the penis below the glans. The cartridge is installed over the exposed glans and under the prepuce with prepuce extended over the cartridge. The anvil is now slid up to the cartridge and secured by the threaded locking ring. At this time, the locking ring is only partially rotated to avoid fully clamping the cartridge.

The excess of prepuce is extended over the cartridge until the desired tension of prepuce is reached. The access windows in the anvil allow for easy access to the prepuce. Now the cartridge can be fully clamped by tightening the locking ring.

The device is fired by turning the knob on the jacking screw in a first direction. At this point, the needles with the suture are fully driven through the skin into the retainers and the knife simultaneously dissects the prepuce.

Upon completion of setting the sutures within the suture retainers and separation of the prepuce, the needles and the knife are removed from the retainers by turning back the knob in the opposite or second direction to retract the cartridge. The device is then removed by unscrewing the locking ring and separating the two anvils halves leaving the suture with the suture retainers attached to the penis. Any suture excess can be trimmed.

The method of circumcising may also include the step of providing the circumcising system in more than one size.

BRIEF DESCRIPTION OF THE DRAWINGS

The accompanying drawings, which are incorporated in and form part of the specification, illustrate the present disclosure when viewed with reference to the description, wherein.

Figure 1:
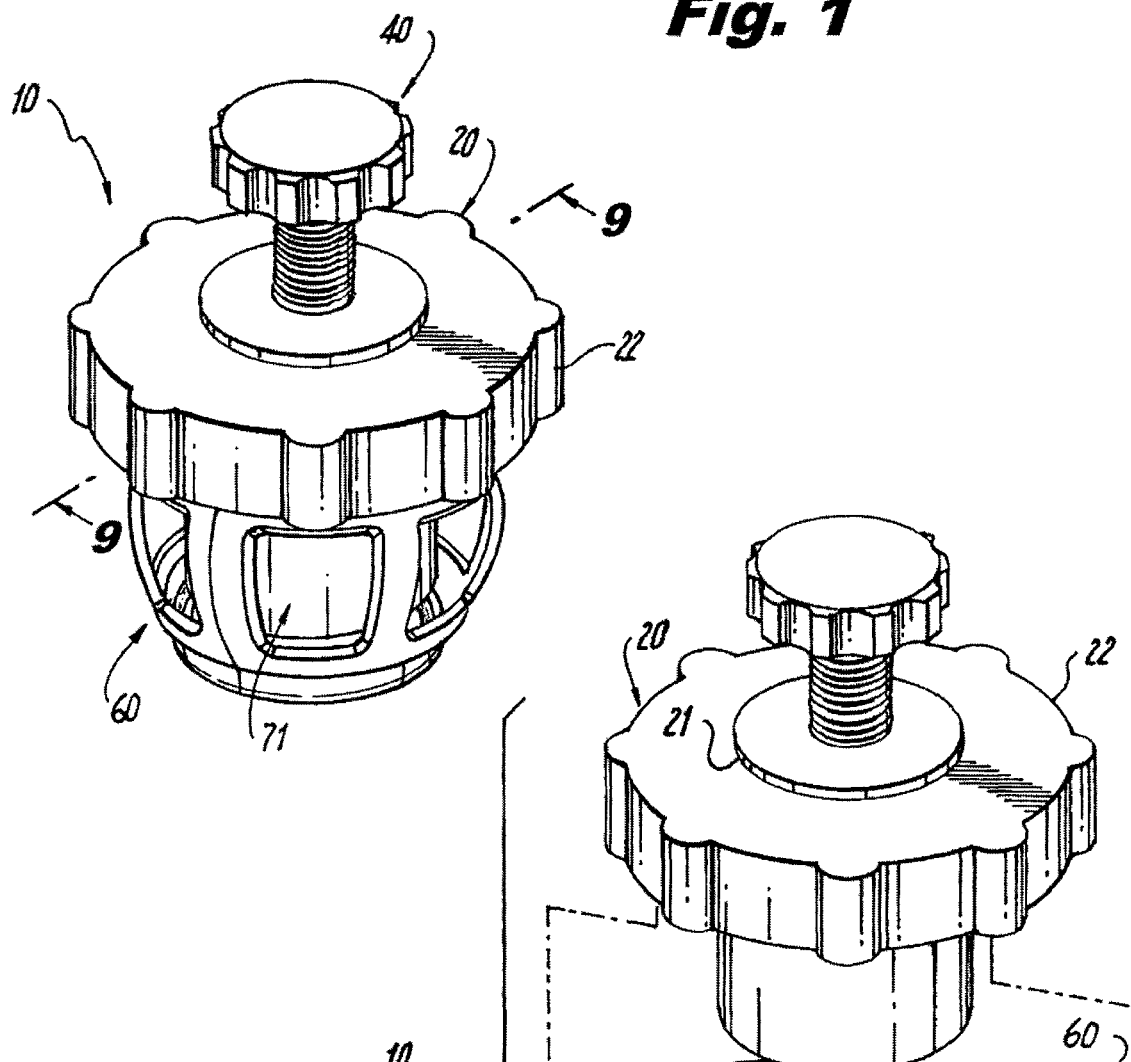
FIG. 1 is a perspective view of a disposable circumcision device in accordance with the principles of the present disclosure, illustrating a housing, actuation mechanism, and an anvil.

Other features of the present disclosure will become apparent from the following detailed description, taken in conjunction with the accompanying drawings, which illustrate, by way of example, the principles of the present disclosure.

DETAILED DESCRIPTION OF THE EMBODIMENTS

Embodiments of the presently disclosed disposable circumcision device and a method for use are described in detail with reference to the drawings, in which like reference numerals designate identical or corresponding elements in each of the several views. As used herein, the term "distal" refers to that portion of the circumcision device, or component thereof, farther from the user while the term "proximal" refers to that portion of the circumcision device or component thereof, closer to the user.

Referring now to the drawings, wherein like reference numerals identify identical or similar structural elements of the subject device throughout the several views, there is illustrated in FIG. 1 a disposable circumcision device, designated generally by reference numeral 10. The disposable circumcision device includes a housing 20, an actuation mechanism 40, a cartridge 43, and an anvil 60.

Figure 2:
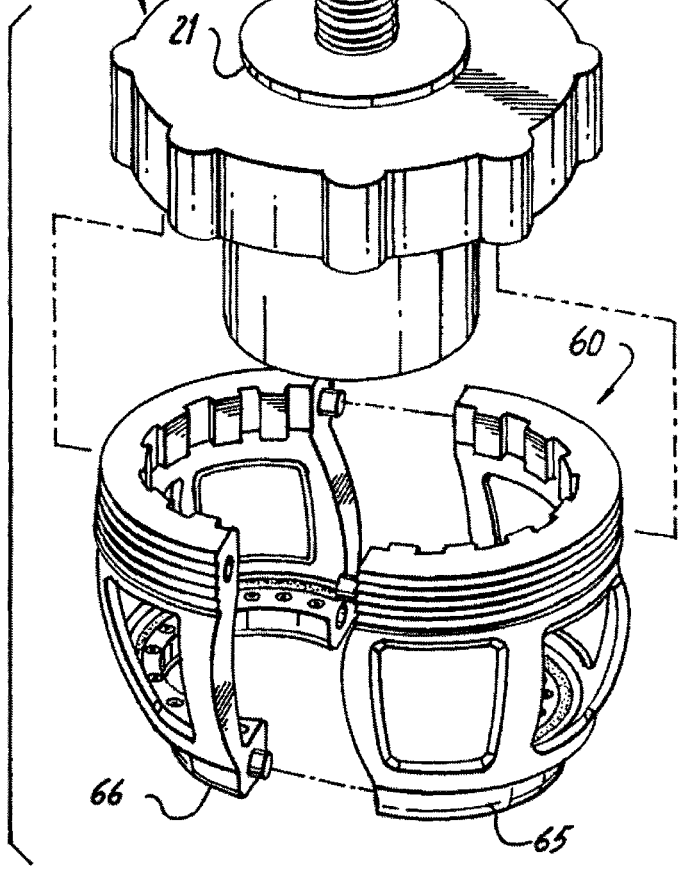
FIG. 2 is a perspective view of the device of FIG. 1, illustrating the two sections of the anvil.
Figure 3:
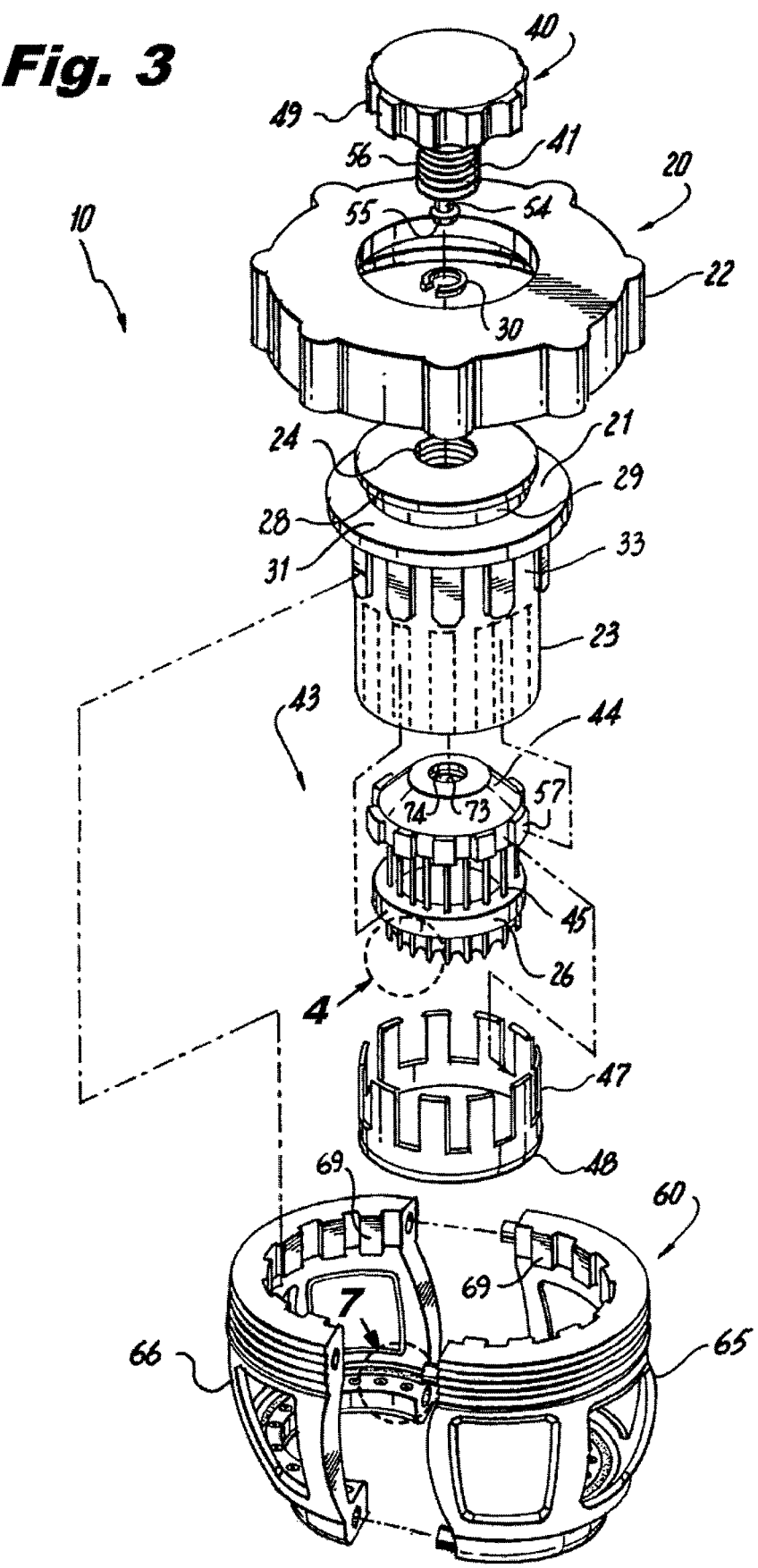
FIG. 3 is an exploded perspective view, with parts separated, of the device of FIGS. 1 and 2.
Figure 4:
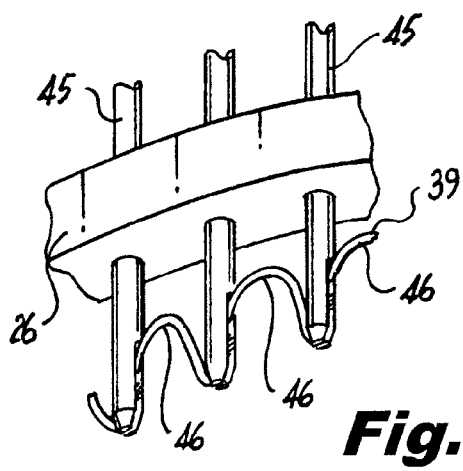
FIG. 4 is an enlarged perspective view of the needle guide, needles, and suture of the device of FIG. 1 taken at the indicated area of FIG. 3.
Figure 9:
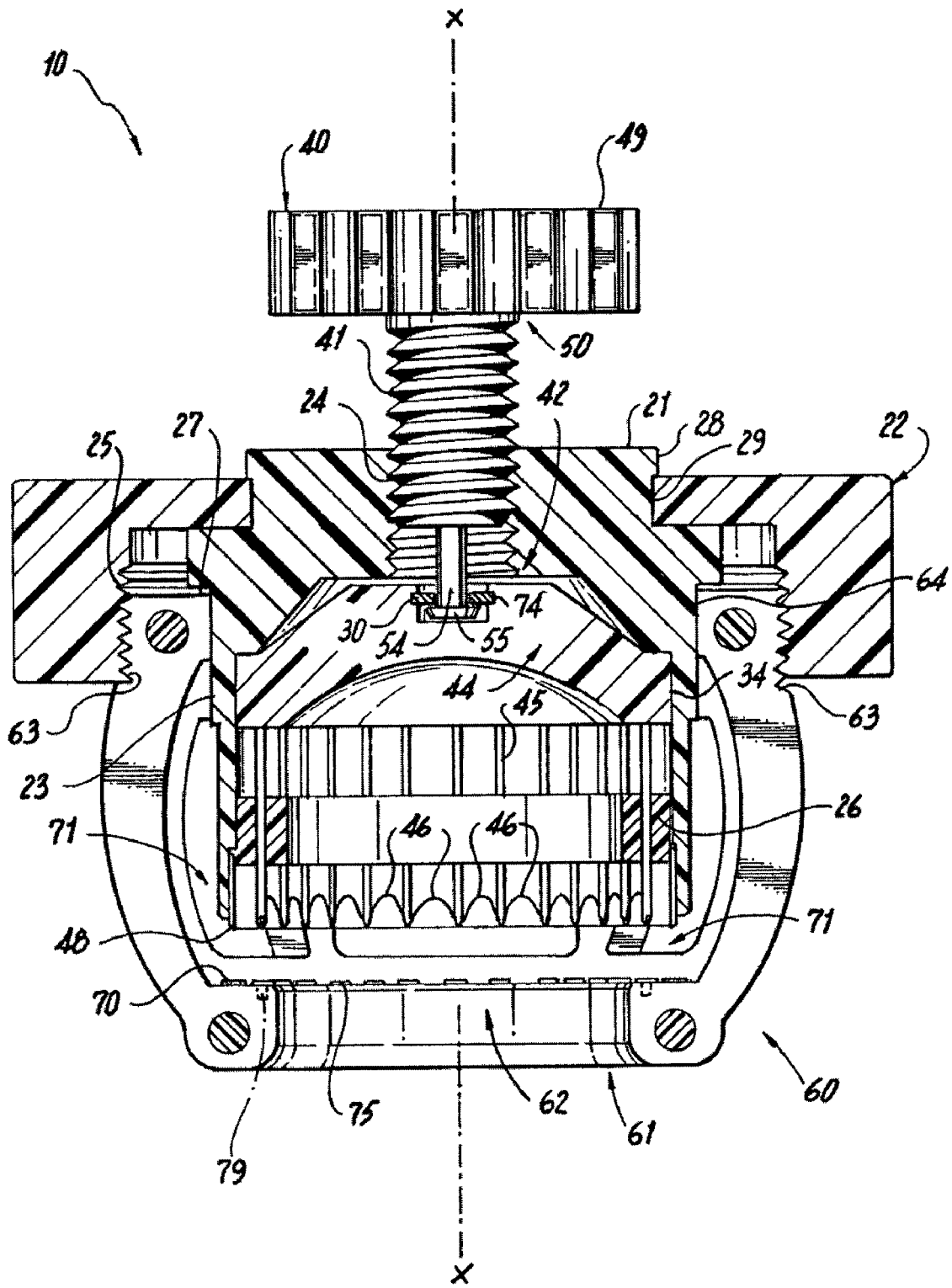
FIG. 9 is a side cross-sectional view of the device of FIG. 1 taken along section line 9-9 of FIG. 1.

Referring now to FIGS. 2, 3, and 9, the housing 20 includes a body 21 and a locking ring 22. The body 21 has a threaded hole 24 that defines a longitudinal axis 'x'-'x'. The body 21 is in the shape of a cylinder, having a retaining flange 28 and a support flange 31 extending radially outward therefrom. A recess 29 separates the retaining flange 28 from the support flange 31.

The body 21 has an external surface 23, as shown in FIG. 3, which is radially inward from and extends distally beyond the locking ring 22. The external surface 23 has a series of external guide grooves 33 about the outer circumference. The locking ring 22 has an inner diameter that is smaller than the outer diameter of either the retaining flange 28 or the support flange 31.

The inner diameter of the locking ring 22 is larger than the outer diameter of the recess 29. As a result, the locking ring 22 is rotatably secured on to the body 21 of the housing 20. The locking ring 22 may be press fit into the body 21. The locking ring 22 has an internal thread 25 located radially outward from the external surface 23 of the body 21.

Referring now to FIG. 9, the actuation mechanism 40 includes a knob 49 fixed to a proximal end 50 of a jacking screw 41. The jacking screw 41 extends through the threaded hole 24 in the body 21. The jacking screw 41 has threads 56 that are complementary to the threaded hole 24 of the housing 20. A stem 54 extends distally from the jacking screw 41. A bulb 55 is located about the distal end of the stem 54.

With continued reference to FIGS. 3 and 9, the cartridge 43 is disposed within the body 21 of the housing 20. The body 21 has a series of internal guide grooves 34 that compliment a series of internal guide protrusions 57 on the cartridge 43. The combination of the internal guide grooves 34 and internal guide protrusions 57 work together to keep the cartridge 43 in a predefined alignment position with respect to the housing 20.

The cartridge 43 is rotatably attached to a distal end 42 of the jacking screw 41 with a retaining ring 30. The retaining ring 30 is located radially outward from the stem 54 and proximally from the bulb 55. The retaining ring 30 is sized to fit about the stem 54; however, bulb 55 is too large to pass through the retaining ring 30.

The cartridge 43 includes a cap 44, a series of needles 45, a length of suture material 39, and a knife 47. The cap 44 has a hole 73 and a retaining recess 74. The hole 73 is sized to be smaller than the retaining ring 30. The retaining recess 74 is sized to accept the retaining ring 30 therein and allow expansion of the retaining ring. The retaining ring 30 is radially compressed as it is pressed into the hole 73 and expands within the retaining recess 74. As a result, the retaining ring 30 is retained within the retaining recess 74 and captures the bulb 55 within the hole 73.

The jacking screw 41 is configured to provide distal movement of the cartridge 43 along the longitudinal axis 'x'-'x' with respect to the housing 20. The cartridge 43 is driven in both directions by the turn of the knob 49. When the knob 49 is turned in a first direction 'a', the cartridge 43 is advanced distally toward the anvil 60. The advancing cartridge 43 simultaneously advances the cap 44, the series of needles 45, the suture material 39, and the knife 47.

Co-pending U.S. patent application Ser. No. 12/689,441 entitled "SUTURE AND RETAINER ASSEMBLY AND SULU" filed on Jul. 19, 2010, and incorporated by reference in its entirety herein discloses a suturing system which can be configured to include one or more of the presently disclosed embodiments described herein.

Figure 5:
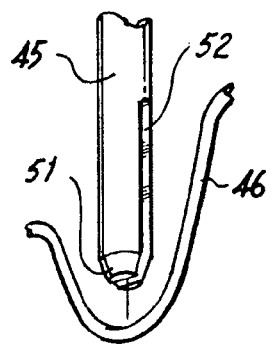
FIG. 5 is an exploded perspective view of the needle and suture.

The series of needles 45 extend distally from inside of the cap 44 and are arranged circularly about the longitudinal axis 'x'-'x'. Now referring to FIG. 5, each of the needles 45 has a tapered proximal end 51 and a groove 52, across the tapered proximal end 51, for receiving and removably retaining a portion of the suture material 39 therein. The needles 45 are arranged such that the groove 52 in each needle 45 is in alignment with the groove 52 of at least one other needle 45 that is located in an adjacent position.

The suture material 39 has a plurality of individual sections or sutures 46. The sutures 46 transition into each other to form loops between each needle 45.

A needle guide 26 may be disposed within the body 21 to stabilize the needles 45 during advancement. Turning the knob 49 in a second direction 'b' returns the cartridge 43 proximally and retracts the cap 44, the series of needles 45 and the knife 47. The knife 47 has a circular blade 48 that is coaxially located about the longitudinal axis 'x'-'x'.

The anvil 60 is in the shape of a collar 61 and has a longitudinal passage 62 that is co-axially located along the longitudinal axis 'x'-'x'.

The anvil 60 has a first section 65 and a second section 66. The first section 65 and the second section 66 form complementary fragments of the collar 61. The first and second sections 65, 66 can be two identical C-shaped pieces. The first section 65 of the anvil 60 has at least one male fitting 67 and the second section 66 of the anvil 60 has at least one female fitting 68. The female fitting 68 accepts and releasably retains the male fitting 67. The male and female fittings 67, 68 may provide a snapping feature that provides interference fit to keep the first and second sections 65, 66 temporarily together to form a single round anvil 60 at assembly. A portion of the external thread 63 is formed about the distal end of each of the first and second sections 65, 66 of the anvil 60. The locking ring 22 secures the first and second sections 65, 66 of the anvil 60 together and to the housing 20.

Figure 7:
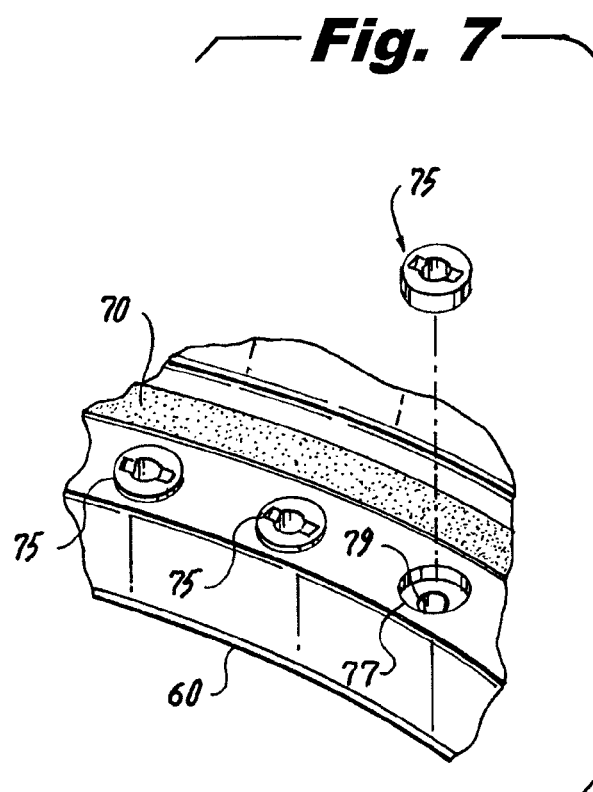
FIG. 7 is an enlarged perspective view of the anvil and suture retainers of the device of FIG. 1 taken at the indicated area of FIG. 3.
Figure 6:
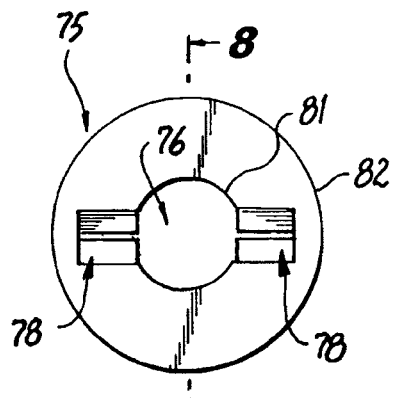
FIG. 6 is a top plan view of the suture retainer.
Figure 8:
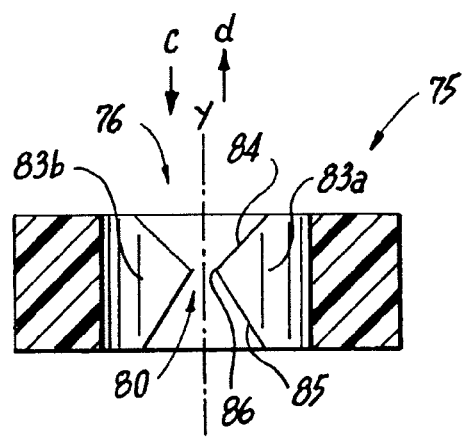
FIG. 8 is a side cross-sectional view of the suture retainer taken along section line 8-8 of FIG. 7.

Referring now to FIGS. 6-8, each section of the anvil 60 has a flat circular portion that forms a cutting ring 70 when the sections are combined. Proximal to the cutting ring 70, the anvil 60 has a series of access windows 71 for accessing the prepuce during assembly of the device 10 over the penis. A series of suture retainers 75 are releasably held within a series of recesses 77 in the anvil 60. The series of suture retainers 75 are arranged circularly about the longitudinal passage 62.

Now referring to FIGS. 6 and 8, each retainer 75 includes a body 82 that defines an aperture 76 therethrough. The shape of the aperture 76 is defined by a central passageway 81, which defines a longitudinal axis 'y' and a pair of diametrically opposed slots 78 extending radially outward from the central passageway 81. The aperture 76 forms a cross-sectional Φ-shaped hole in the body 82 defined by a substantially circular center and two opposed rectangles extending radially outward therefrom. The central passageway 81 has a substantially constant cylindrical shape sized to allow passage of the needle 45 therethrough. Each central passageway 81 is aligned with a hole 79 in the anvil 60 that removably accepts one of the needles 45 therein.

A tortured path section 80 is defined by two protrusions 83a, 83b that extend from slots 78. Each protrusion 83a, 83b extends from one of the sidewalls of the slots 78. Each of the two protrusions 83a, 83b has a proximal surface 84, a distal surface 85, and an apex 86. The proximal surface 84 forms an angle with respect to the longitudinal axis 'y' that is greater than an angle formed by the distal surface 85 intersecting with the longitudinal axis 'y'. As a result, the area of the distal surface 85 is larger than the area of the proximal surface 84. The tortured path section 80 permits passage of the portion of suture 46 in a first direction 'c' and inhibits passage of the portion of suture 46 in a second direction 'd'.

An external thread 63 is located about the anvil 60 and is complimentary to the internal thread 25 on the locking ring 22. The anvil 60 has an internal surface 64 that is configured to be complementary to the external surface 23 of the housing 20. External guiding protrusions 69 on the first and second sections 65, 66 of the anvil 60 align with the external guide grooves 33 on the external surface 23 of the body 21, to assure proper alignment of the needles 45 with the corresponding suture retainers 75. The housing 20 has a stop 27 that prevents the external thread 63 from penetrating past a predetermined depth into the housing 20.

Both the suture 46 and the suture retainer 75 may be constructed from a biocompatible material that is absorbable.

Figure 10:
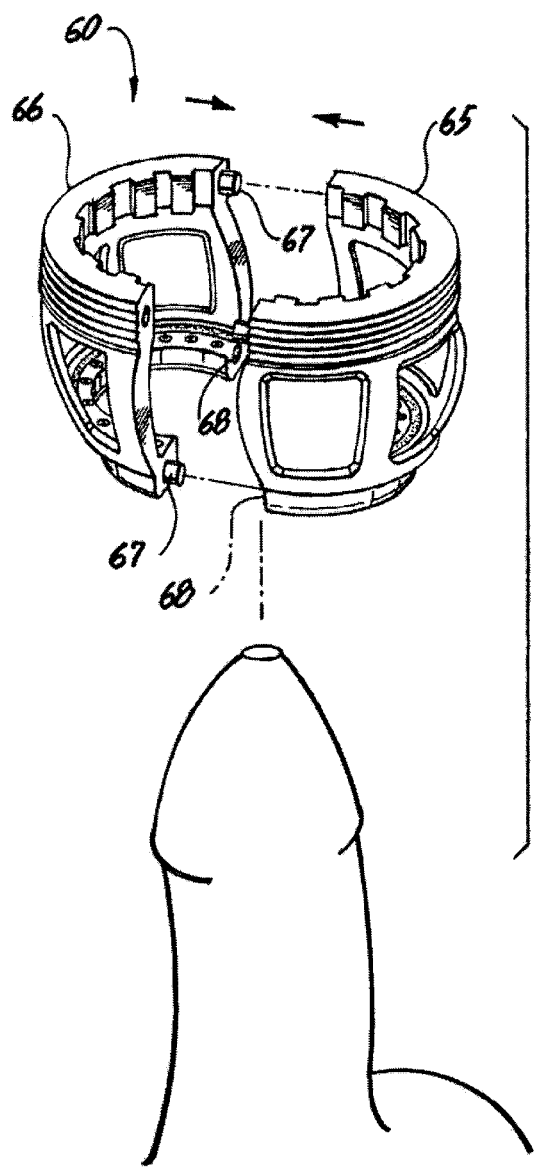
FIG. 10 is a perspective view of the two sections of the anvil being assembled over a penis.
Figure 11:
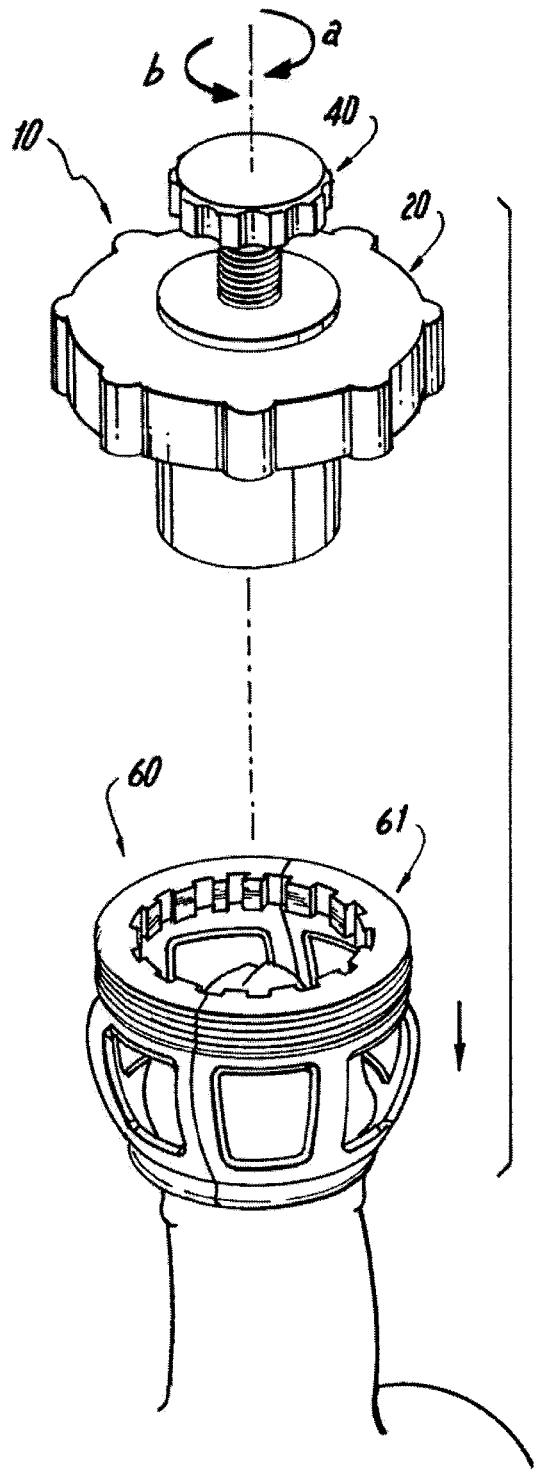
FIG. 11 is a perspective view of the anvil in the shape of a collar placed over the penis.
Figure 12:
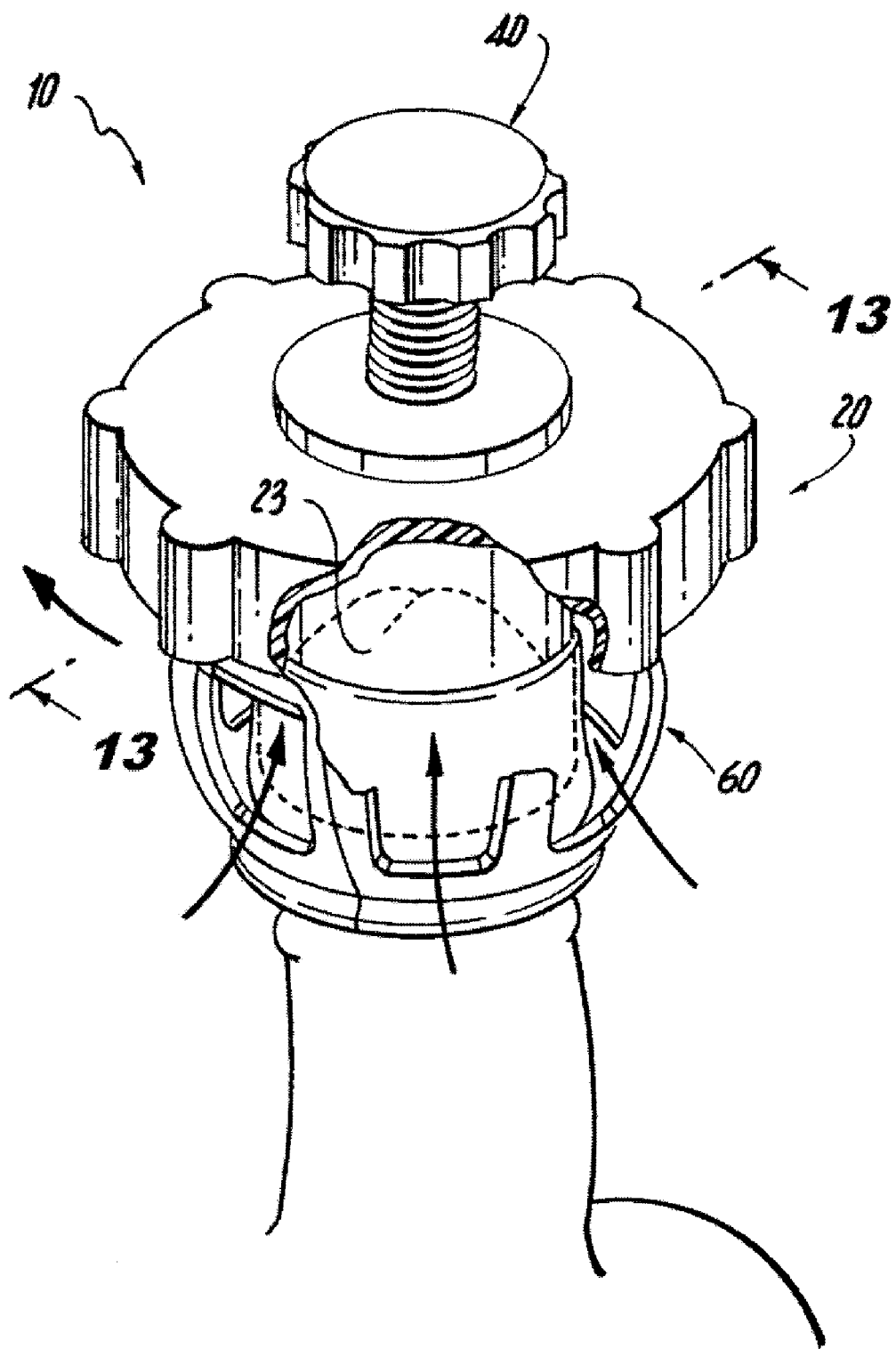
FIG. 12 is a cut away view illustrating the prepuce extended proximally over the distal body portion of the housing.

Referring now to FIGS. 10-12, a method of use of the disposable circumcision device to circumcise a penis to remove an excess of foreskin or prepuce from the penis is also provided. The surgeon is provided with the disposable circumcision device. The first and second sections 65, 66 of the anvil 60 are snapped together and slid down over the penis below the glans. The housing 20 is installed over the exposed glans and under the prepuce with the prepuce being placed over part of the housing 20. The anvil 60 is now slid up to the cartridge 43 and secured by the threaded locking ring 22. At this time, the locking ring 22 is only partially rotated to avoid fully clamping the cartridge 43.

Figure 13:
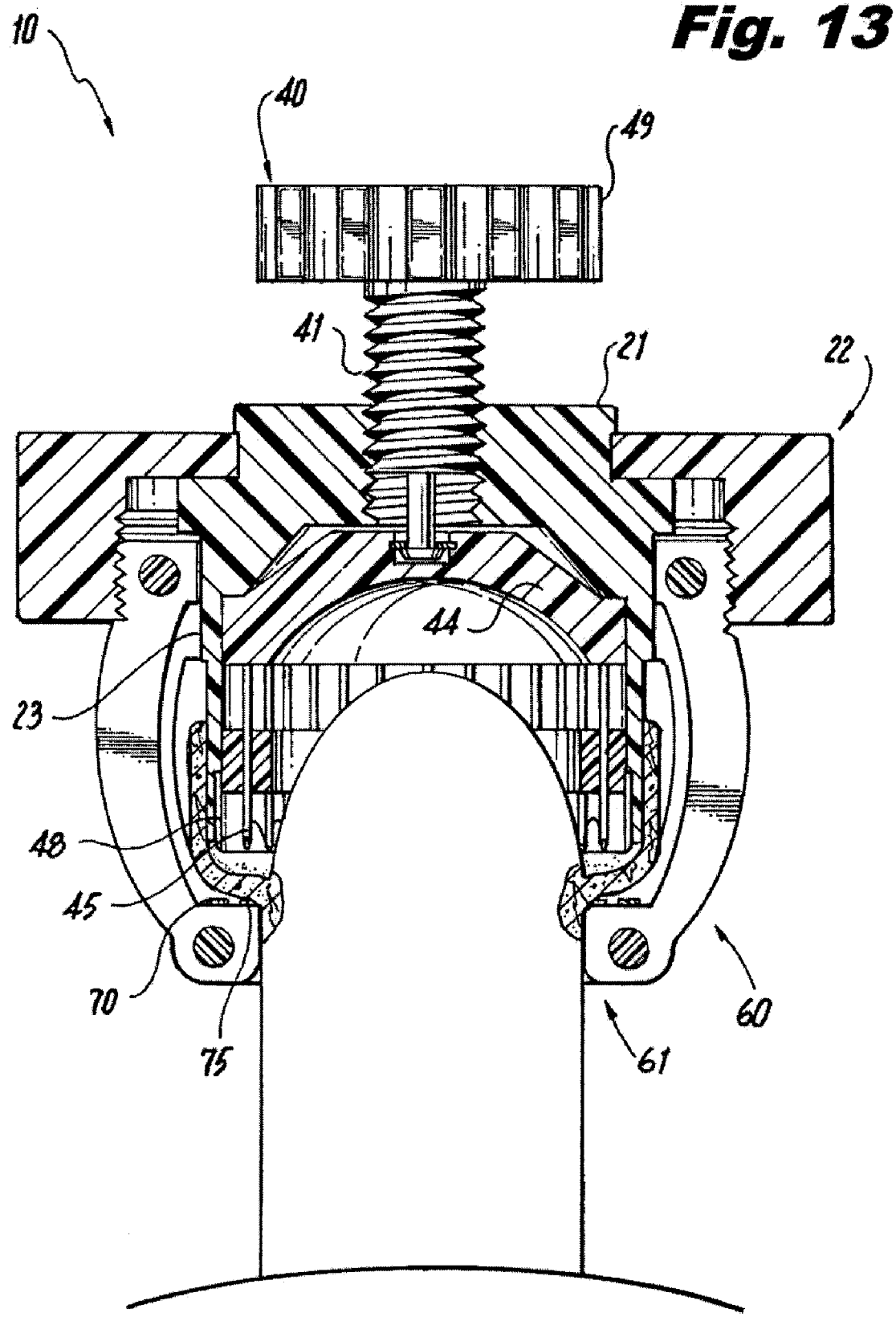
FIG. 13 is a partial side cross-sectional view illustrating the prepuce extended proximally over the distal body portion of the housing taken along section lines 13-13 of FIG. 12.

Referring now to FIG. 13, the excess of prepuce is fully extended over the cartridge 43 until the desired tension of prepuce is reached. The access windows 71 in the anvil 60 allow for easy access to the prepuce. Now the cartridge 43 can be fully clamped by tightening the locking ring 22.

Figure 14:
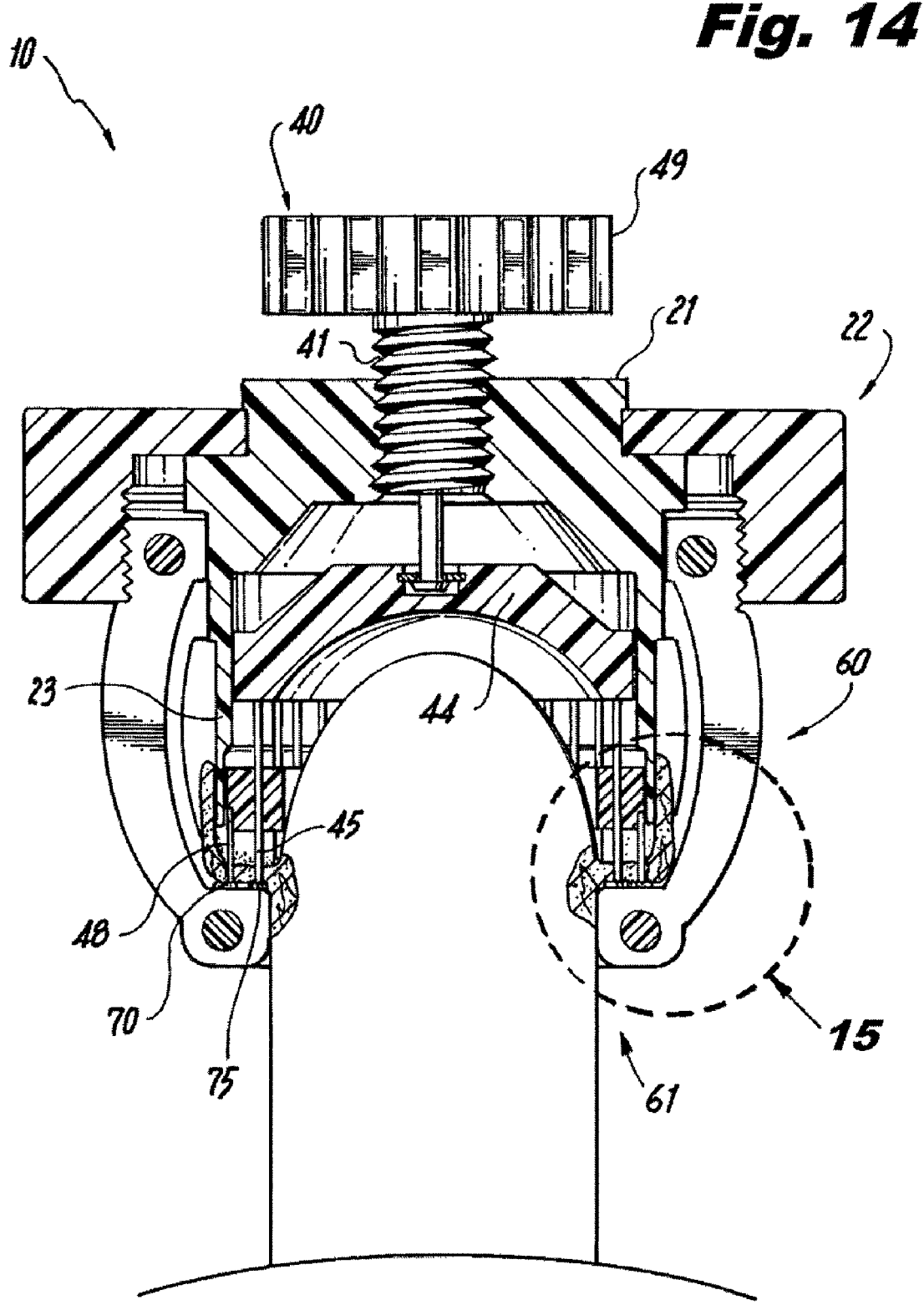
FIG. 14 is a partial side cross-sectional view illustrating the firing of the device and the separation of the prepuce from the penis.
Figure 15:
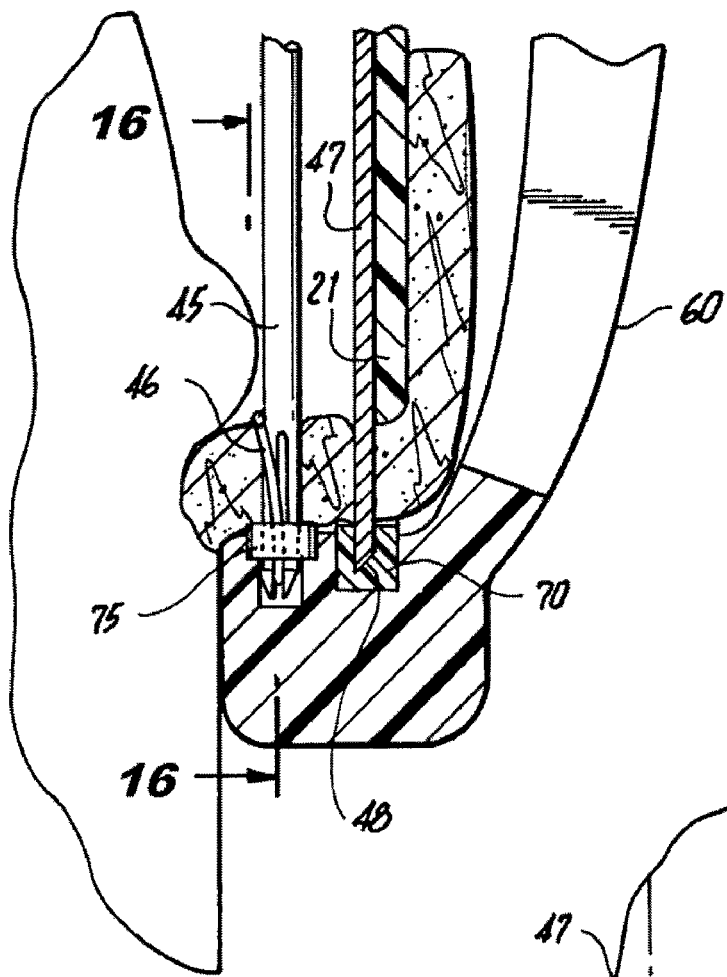
FIG. 15 is a partial side cross-sectional view illustrating the needle and knife in an advanced position of the device of FIG. 1 taken at the indicated area of FIG. 14.
Figure 16:
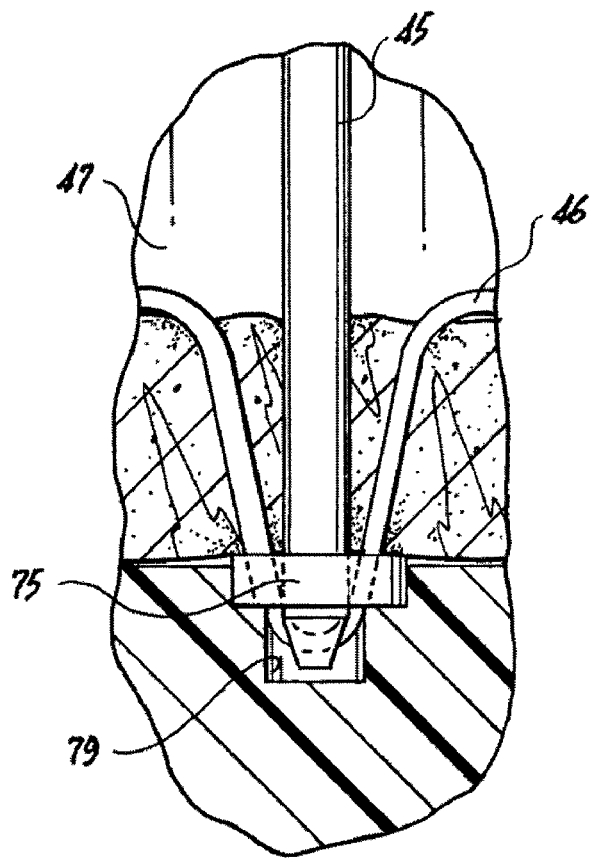
FIG. 16 is a cross-sectional view of a needle and a suture disposed within tissue of FIG. 1 taken along section line 16-16 of FIG. 15.

Referring now to FIGS. 14-16, the device is fired by turning the knob 49 in the first direction 'a' to the very end. When the cartridge 43 is distally disposed, the needles 45 with the suture 46 are fully driven through the skin and into the retainers 75, as the knife 47 dissects the prepuce from the penis. As a result, the penis is sutured and circumcised, simultaneously.

Figure 17:
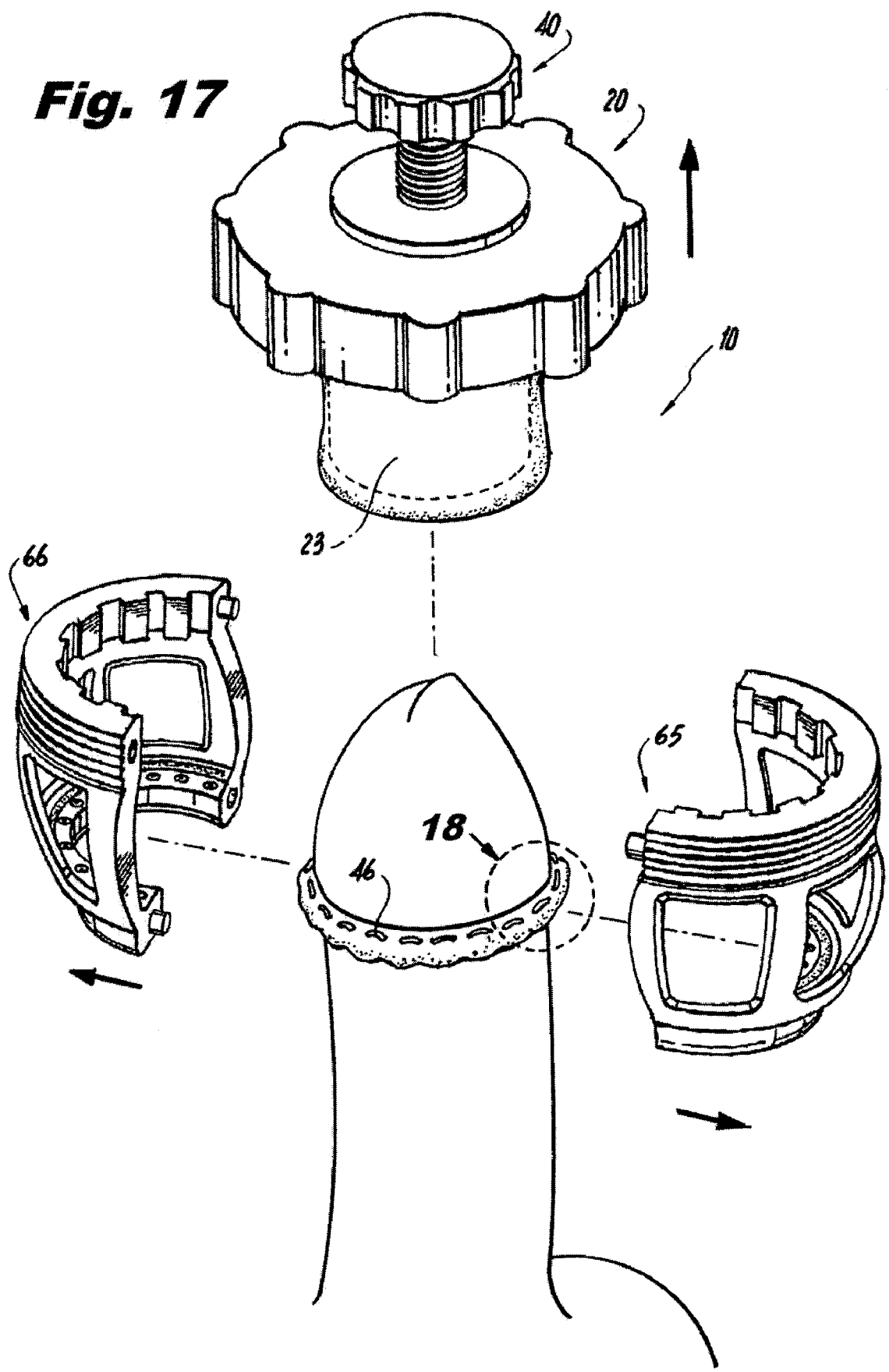
FIG. 17 is a perspective view illustrating separation of the sections of the anvil from each other and from the housing.

Referring now to FIG. 17, upon completion of setting the suture 46 within the suture retainers 75 and separation of the prepuce, the needles 45 and the knife 47 are removed from the retainers 75 by turning the knob 49 in the opposite or second direction 'b' to retract the cartridge 43. The device is then removed by unscrewing the locking ring 22 and separating the two anvil sections 65, 66 leaving the suture 46 within the suture retainers 75 about the penis. Any suture 46 excess may then be trimmed.

Figure 18:
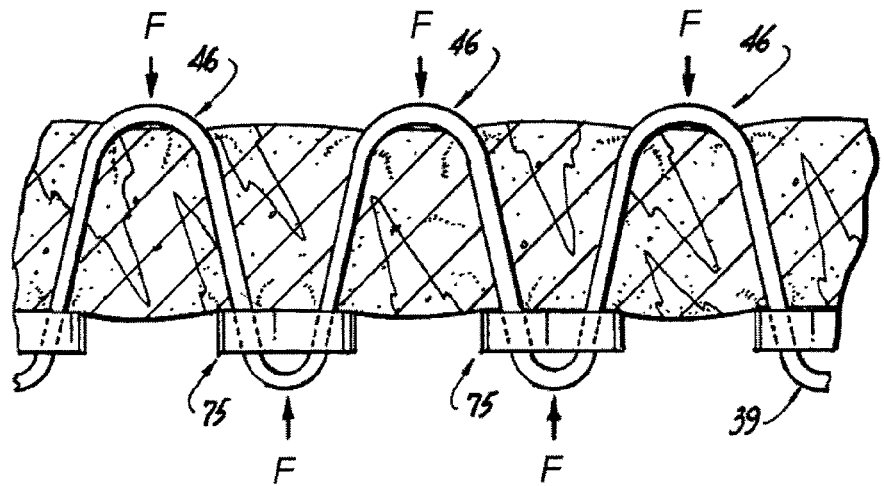
FIG. 18 is a side, partial cut away view illustrating a suture being restrained by a suture retainer within tissue of the device of FIG. 1 taken at the indicated area of FIG. 18.

Referring now to FIG. 18, the suture 46 is secured within the suture retainers 75 and holds the tissue together by the application of force "F".

Figure 19:
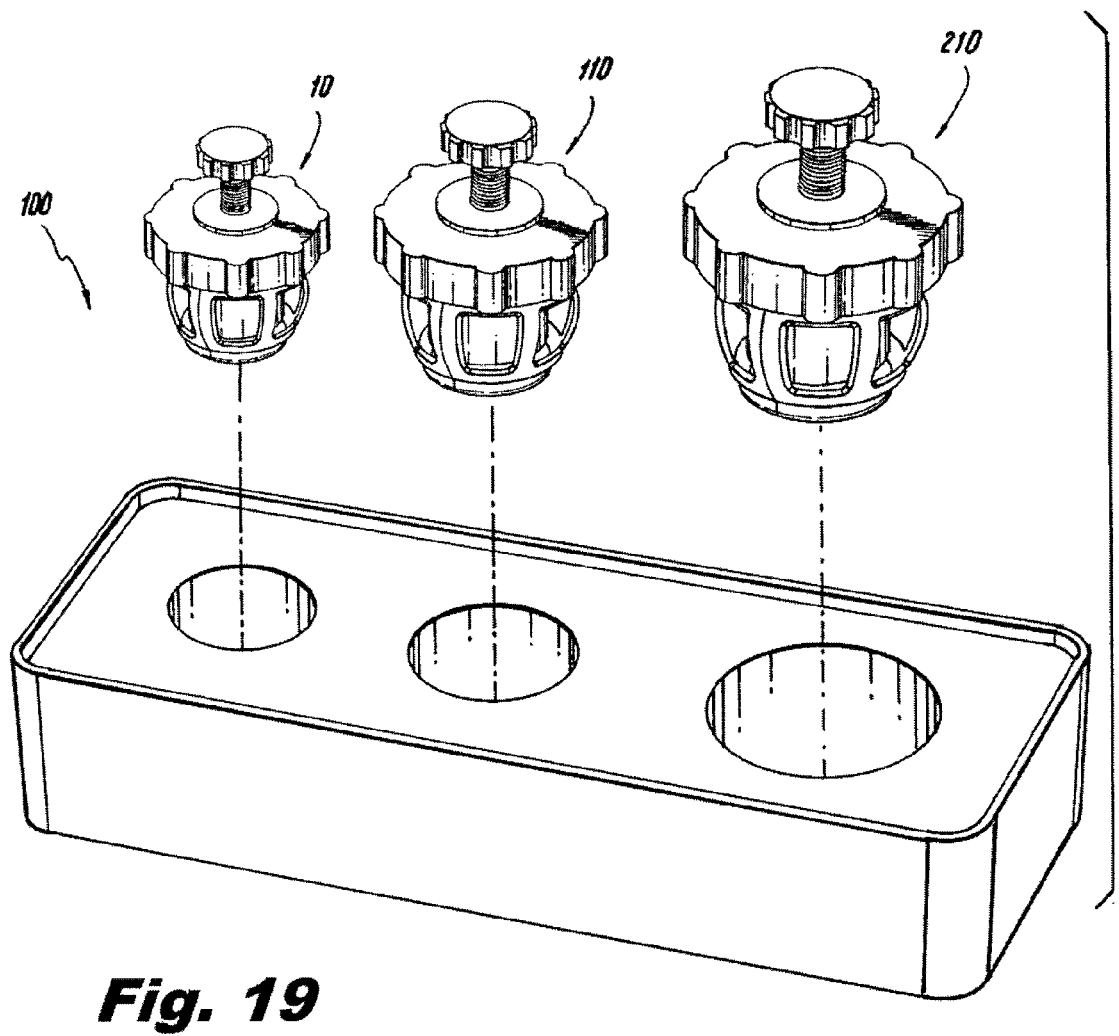
FIG. 19 is a perspective view of a kit of devices in accordance with the principles of another embodiment of the present disclosure.

Referring now to FIG. 19, the method of circumcising may also include the step of providing the circumcising system 5 in more than one size. The kit 100 may include a small circumcising system 10, a medium circumcising system 110, and a large circumcising system 210.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A circumcision system for removing tissue from a penis, comprising:
a housing having a threaded hole that defines a longitudinal axis and a locking ring, the locking ring having an internal thread;
an actuation mechanism extending through the threaded hole, the actuation mechanism having a series of needles, the series of needles operably coupled to the actuation mechanism and extending distally therefrom, the actuation mechanism configured to provide longitudinal movement of the needles with respect to the housing;

a suture removably attached to a distal end of each of the series of needles;

an anvil having a passage that is located co-axially with the longitudinal axis and an external thread that is configured to be complimentary to the internal thread, the anvil being in the shape of a collar;

a knife having a circular blade connected to the actuation mechanism; and a suture retainer releasably attached to the anvil.

2. The circumcision system of claim 1, wherein the suture and the suture retainer are constructed from a biocompatible material that is absorbable.

3. The circumcision system of claim 1, wherein each of the series of needles has a tapered end and a groove through the tapered end configured to accept and detachably retain the suture.

4. The circumcision system of claim 3, wherein:

the suture retainer has a passageway, the passageway defining a substantially cylindrical bore and diametrically opposed slots extending radially outward therefrom, the substantially cylindrical bore being configured to removably accept one of the needles therethrough, the diametrically opposed slots having a restricted section configured to secure the suture during and after removal of the needles from the suture retainer.

5. The circumcision system of claim 1, further comprising a cartridge attached at the distal end of the actuation mechanism, the housing the series of needles disposed in the cartridge.

6. The circumcision system of claim 1, wherein the anvil has a first section and a second section, each of the first section and the second section are complementary fragments that mount together to form the shape of the collar.

7. The circumcision system of claim 6, wherein the first section of the anvil has a male fitting and the second section of the anvil has a female fitting, wherein the female fitting is configured to accept and releasably retain the male fitting.

8. The circumcision system of claim 7, wherein a portion of the external thread is formed about a proximal end of each of the first and second sections of the anvil.

9. The circumcision system of claim 1, wherein the anvil has a series of access windows.

10. The circumcision system of claim 1, wherein the housing has a stop that prevents the external thread from penetrating past a predetermined depth into the housing.

11. The circumcision system of claim 10, wherein the housing has guide groove to ensure proper positioning of the anvil with respect to the series of needles.

12. The circumcision system of claim 1, wherein the housing has an external surface, the anvil has an internal surface that is configured to be complement intimately with the external surface of the housing.

13. The circumcision system of claim 1, wherein the suture has the shape of a ring.

14. The circumcision system of claim 1, wherein the grooves in the needles are aligned circularly.

15. The circumcision system of claim 1, wherein the actuation mechanism is a jacking screw.

16. The circumcision system of claim 1, wherein the anvil further comprises a cutting ring.

* * * * *